(12) United States Patent
Janzig (10) Patent No.: US 9,168,376 B2
(45) Date of Patent: Oct. 27, 2015

(54) IMPLANTABLE DEVICE WITH OPPOSING LEAD CONNECTORS

(71) Applicant: MEDTRONIC, INC., Minneapolis, MN (US)

(72) Inventor: Darren A. Janzig, Center City, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 14/210,879

(22) Filed: Mar. 14, 2014

(65) Prior Publication Data

US 2014/0277216 A1    Sep. 18, 2014

Related U.S. Application Data

(60) Provisional application No. 61/789,227, filed on Mar. 15, 2013.

(51) Int. Cl.
*A61N 1/375*    (2006.01)
*A61N 1/36*    (2006.01)

(52) U.S. Cl.
CPC ............ *A61N 1/3605* (2013.01); *A61N 1/3752* (2013.01)

(58) Field of Classification Search
CPC .......................... A61N 1/375; A61N 1/3752
See application file for complete search history.

(56) References Cited

U.S. PATENT DOCUMENTS

| 4,262,982 | A | 4/1981 | Kenny |
| 4,934,366 | A | 6/1990 | Truex |
| 6,327,502 | B1 * | 12/2001 | Johansson et al. ............. 607/36 |
| 7,515,964 | B1 | 4/2009 | Alexander |
| 7,563,141 | B2 | 7/2009 | Alexander |
| 7,711,427 | B2 | 5/2010 | Janzig |
| 7,711,428 | B2 | 5/2010 | Janzig |
| 7,890,175 | B1 | 2/2011 | Rey |
| 8,131,370 | B2 | 3/2012 | Janzig |
| 8,738,141 | B2 | 5/2014 | Smith |
| 2007/0179553 | A1 | 8/2007 | Iyer |
| 2011/0004279 | A1 | 1/2011 | North |
| 2014/0277217 | A1 | 9/2014 | Janzig |
| 2014/0277218 | A1 | 9/2014 | Janzig |

FOREIGN PATENT DOCUMENTS

EP    11246101 B1    7/2004

OTHER PUBLICATIONS

International Search Report and Written Opinion for PCT/US2014/027202 mailed Jun. 30, 2014.

* cited by examiner

*Primary Examiner* — George Evanisko
(74) *Attorney, Agent, or Firm* — Mueting, Raasch & Gebhardt, P.A.

(57) ABSTRACT

An implantable active medical device includes a chassis plate and a first and second elongate lead connector fixed to and extending orthogonally away from the chassis plate in opposing directions. The first and second elongate lead connectors are disposed within hermetic housings.

19 Claims, 5 Drawing Sheets

IMPLANTABLE DEVICE WITH OPPOSING LEAD CONNECTORS

CROSS-REFERENCE

This application claims the benefit of U.S. Provisional Application Ser. No. 61/789,227, filed Mar. 15, 2013, the disclosure of which is incorporated herein by reference.

BACKGROUND

Implantable active medical devices, such as cardiac rhythm management devices (pacemakers and defibrillators) and a variety of implantable muscle/nerve stimulators, for example, generally include a battery and battery-powered electronic pulse generator contained within a hermetically sealed housing or case and attached to a lead connector housing or block. The lead connector block is often affixed to the hermetically sealed housing with brackets, metal solder, laser or resistance welding, pins, screws, other fasteners and/or a medical grade adhesive. The method of fixation requires extensive design and load testing to ensure adequate fixation. The function of the lead connector block is to electrically and mechanically couple the electronic pulse generator with the therapy lead. The lead connector block is typically attached to the exterior of the hermetically sealed housing and is significant to defining the overall device shape and volume. Most often with each new device design, a new lead connector block must also be designed requiring substantial project resources and project schedule.

The electronics within the hermetically sealed housing are conductively coupled to the lead connector block with an electrical feedthrough assembly. Electrical feedthroughs serve the purpose of providing a conductive path extending between the interior of a hermetically sealed container and a point outside the hermetically sealed housing that ultimately connects to the electrical contacts that interface with the therapy lead connector rings. The conductive path through the feedthrough usually includes a conductor pin or terminal that is electrically insulated from the hermetically sealed housing and hermetically bonded to a feedthrough housing or ferrule. The feedthrough housing is hermetically assembled to the device housing most often by laser welding. While this arrangement has proven to be highly reliable, it involves a variety of expensive manufacturing processes and parts that necessarily increase the cost and overall volume of the resulting product and limit device shape and/or configuration.

Ongoing efforts by the industry to reduce the size of the implantable device are desired. Early implantable pacemakers back in the 1960's were about the size of a hockey puck. With advances in microelectronics and integrated circuitry, significantly more features and capabilities have been embodied in implantable active medical devices that can be very small. Nonetheless, efforts to further reduce the size of implantable active medical devices continue in the industry.

BRIEF SUMMARY

The present disclosure relates to an implantable medical device having a chassis element and elongate lead connectors fixed to the chassis element and extending in opposite direction away from the chassis element.

In one illustrative embodiment, an implantable active medical device includes a chassis plate having a first major surface and an opposing second major surface and the chassis plate extends between a chassis first end region and a chassis second end region. A first elongate lead connector is fixed to the first major surface and extends orthogonally away from the first major surface. A second elongate lead connector is fixed to the second major surface and extends orthogonally away from the second major surface. A first hermetic housing defines a first sealed housing cavity. The first hermetic housing is fixed to the first major surface and the first elongate lead connector is disposed within the first sealed housing cavity. A second hermetic housing defines a second sealed housing cavity. The second hermetic housing is fixed to the second major surface and the second elongate lead connector is disposed within the second sealed housing cavity.

In another illustrative embodiment, an implantable active medical device includes a chassis plate having a first major surface and an opposing second major surface and the chassis plate extends between a chassis first end region and a chassis second end region. A first elongate lead connector is fixed to the first major surface and extends orthogonally away from the first major surface. A second elongate lead connector is fixed to the second major surface and extends orthogonally away from the second major surface. A first housing defines a first housing cavity. The first housing is fixed to the first major surface and a power source and the first elongate lead connector are disposed within the first housing cavity. A second housing defines a second housing cavity. The second housing is fixed to the second major surface and a circuit board and the second elongate lead connector are disposed within the second housing cavity.

These and various other features and advantages will be apparent from a reading of the following detailed description.

BRIEF DESCRIPTION OF THE DRAWINGS

The disclosure may be more completely understood in consideration of the following detailed description of various embodiments of the disclosure in connection with the accompanying drawings, in which.

The figures are not necessarily to scale. Dashed or broken lines indicate internal structure or structure covered by solid surfaces. Like numbers used in the figures refer to like components. However, it will be understood that the use of a number to refer to a component in a given figure is not intended to limit the component in another figure labeled with the same number.

DETAILED DESCRIPTION

In the following description, reference is made to the accompanying set of drawings that form a part hereof and in which are shown by way of illustration several specific embodiments. It is to be understood that other embodiments are contemplated and may be made without departing from the scope or spirit of the present disclosure. The following detailed description, therefore, is not to be taken in a limiting sense.

Unless otherwise indicated, all numbers expressing feature sizes, amounts, and physical properties used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings disclosed herein.

As used in this specification and the appended claims, the singular forms "a", "an", and "the" encompass embodiments having plural referents, unless the content clearly dictates otherwise. As used in this specification and the appended claims, the term "or" is generally employed in its sense including "and/or" unless the content clearly dictates otherwise.

Spatially related terms, including but not limited to, "lower", "upper", "beneath", "below", "above", and "on top", if used herein, are utilized for ease of description to describe spatial relationships of an element(s) to another. Such spatially related terms encompass different orientations of the device in use or operation in addition to the particular orientations depicted in the figures and described herein. For example, if an element depicted in the figures is turned over or flipped over, portions previously described as below or beneath other elements would then be above those other elements.

As used herein, when an element, component or layer for example is described as being "on" "connected to", "coupled with" or "in contact with" another element, component or layer, it can be directly on, directly connected to, directly coupled with, in direct contact with, or intervening elements, components or layers may be on, connected, coupled or in contact with the particular element, component or layer, for example. When an element, component or layer for example is referred to as begin "directly on", "directly connected to", "directly coupled with", or "directly in contact with" another element, there are no intervening elements, components or layers for example.

The present disclosure relates to an implantable medical device having a chassis element. In particular the present disclosure relates to an implantable medical device having a chassis element and elongate lead connectors fixed to the chassis element and extending in opposite direction away from the chassis element. The chassis element provides a rigid support structure that maintains the displacement between components fixed to the chassis element minimizing the amount of strain relief needed between those components. The chassis element also enables the use of multiple or different battery options based on the specific therapy indication. The chassis element also provides access to at least two sides of the functional elements within the device. The opposing lead connectors allows for convenient cable management by being able to wind the leads or lead extensions in opposing directions around the device, particularly during the implant procedure. For example, this opposing lead connector design facilitates lead management at an implant site. While the present disclosure is not so limited, an appreciation of various aspects of the disclosure will be gained through a discussion of the examples provided below.

Figure 1:
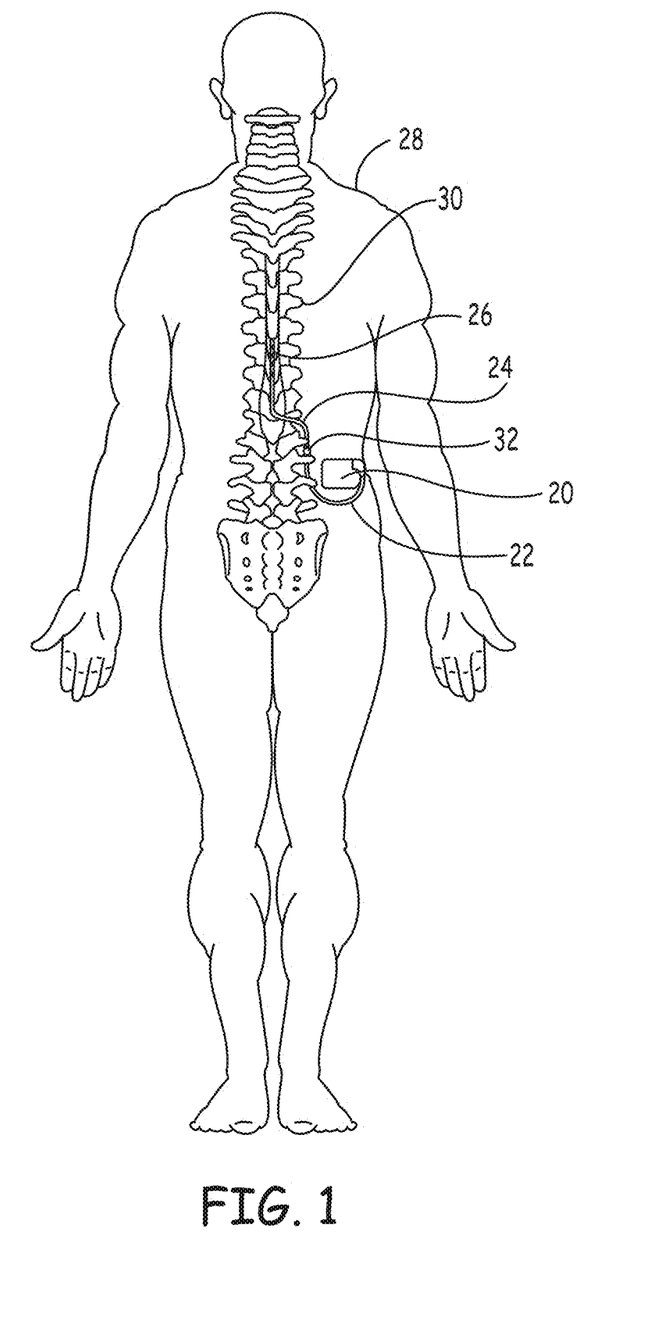
FIG. 1 is a schematic diagram of a an active medical device implanted within a human body.

FIG. 1 is a schematic diagram of an active medical device 20 implanted within a human body or patient 28. The implanted active medical device 20 is illustrated as a neurostimulator, however, the implanted active medical device 20 can be any "active implantable medical device" or "implantable signal generator" as described above and can be placed in any location within a body cavity or tissue within the body, or on the surface of a patient's skin, as desired.

The active medical device 20 is coupled to a lead extension 22 having a proximal end coupled to the active medical device 20, and a lead 24 having a proximal end coupled to a distal end 32 of the lead extension 22 and a distal end of the lead 24 coupled to one or more electrodes 26. In other embodiments, the lead 24 proximal end is coupled to the active medical device 20, without a need for a lead extension 22. The active medical device 20 can be implanted in any useful region of the body such as in the abdomen of a patient 28, and the lead 24 is shown placed somewhere along the spinal cord 30. Particularly useful active medical devices 20 for this disclosure are coupled to at least two leads or lead extensions.

In many embodiments, the active medical device 20 has two leads each having four to eight electrodes or more electrodes. Such a system may also include a physician programmer and a patient programmer (not shown). The active medical device 20 can be considered to be an implantable signal generator of the type available from Medtronic, Inc. and capable of generating multiple signals occurring either simultaneously or one signal shifting in time with respect to the other, and having independently varying amplitudes and signal widths. The active medical device 20 contains a power source and the electronics for sending precise, electrical signals to the patent to provide the desired treatment therapy. While the active medical device 20, in many embodiments, provides electrical stimulation by way of signals, other forms of stimulation may be used as continuous electrical stimulation.

In many embodiments, each lead 24 is a wire having insulation thereon and includes one or more insulated electrical conductors each coupled at their proximal end to a connector ring and to contacts/electrodes 26 at its distal end. Some leads are designed to be inserted into a patient percutaneously (e.g. the Model 3487A Pisces-Quad® lead available from Medtronic, Inc.), and some are designed to be surgically implanted (e.g. Model 3998 Specify® lead, also available form Medtronic, Inc.). In some embodiments, each lead 24 may contain a paddle shape at its distal end for housing electrodes 26. In many embodiments, electrodes 26 may include one or more ring electrodes at the distal end of lead 24.

Figure 2:
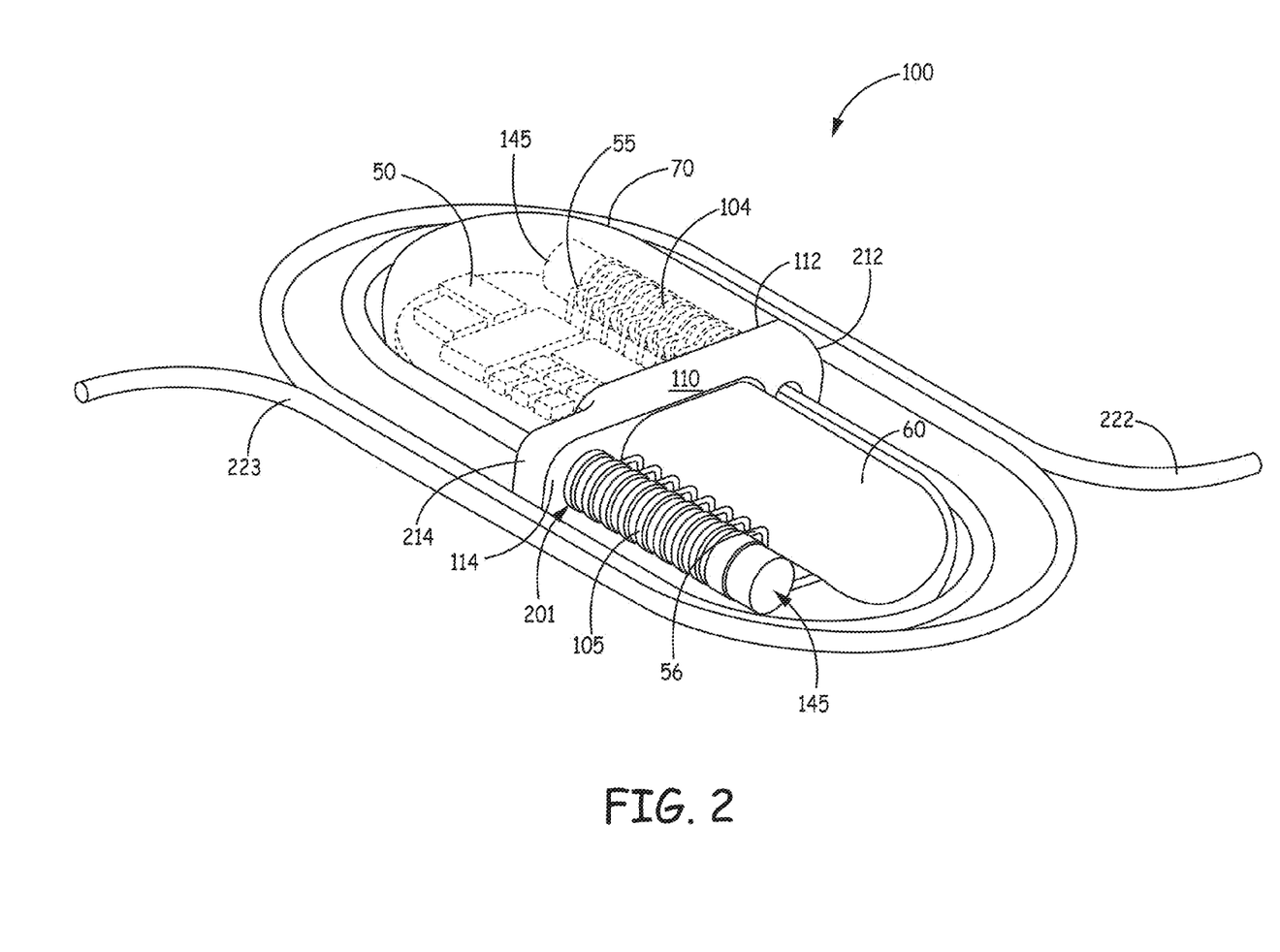
FIG. 2 is a schematic perspective view of an implantable active medical device with opposing internal hermetic lead connectors with the hermetic housings shown transparent for illustration.
Figure 3:
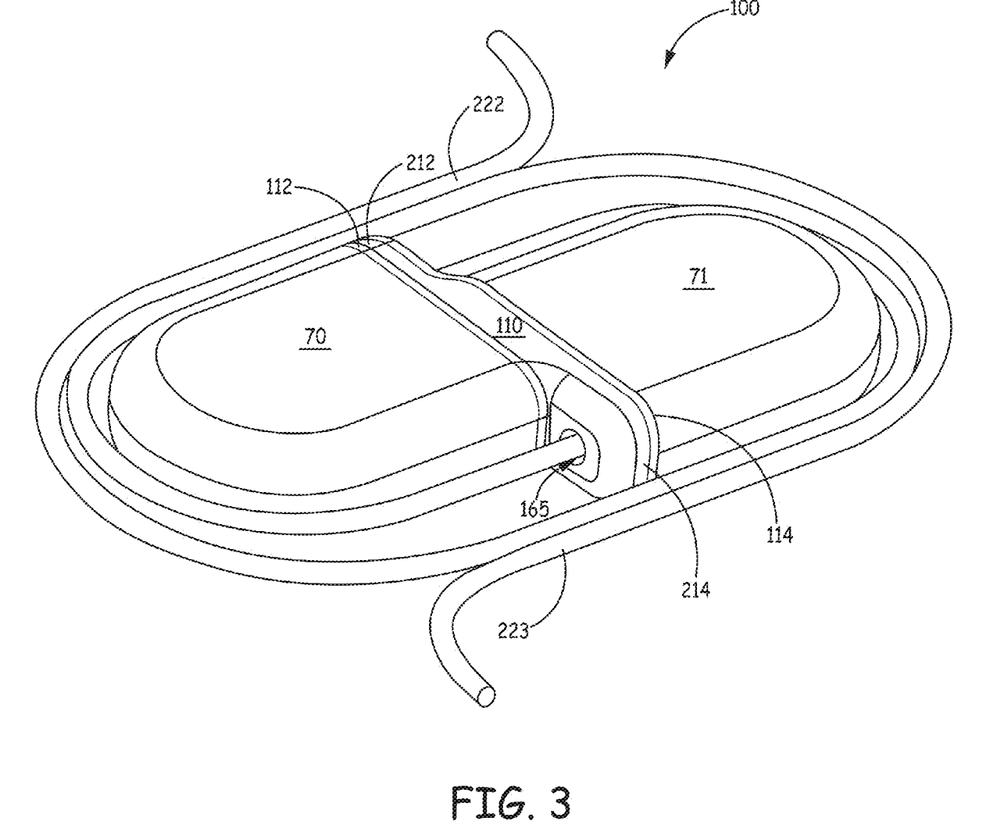
FIG. 3 is a schematic perspective view of the implantable active medical device of FIG. 2 with the hermetic housings in place and two leads engaged with the lead connectors.
Figure 4:
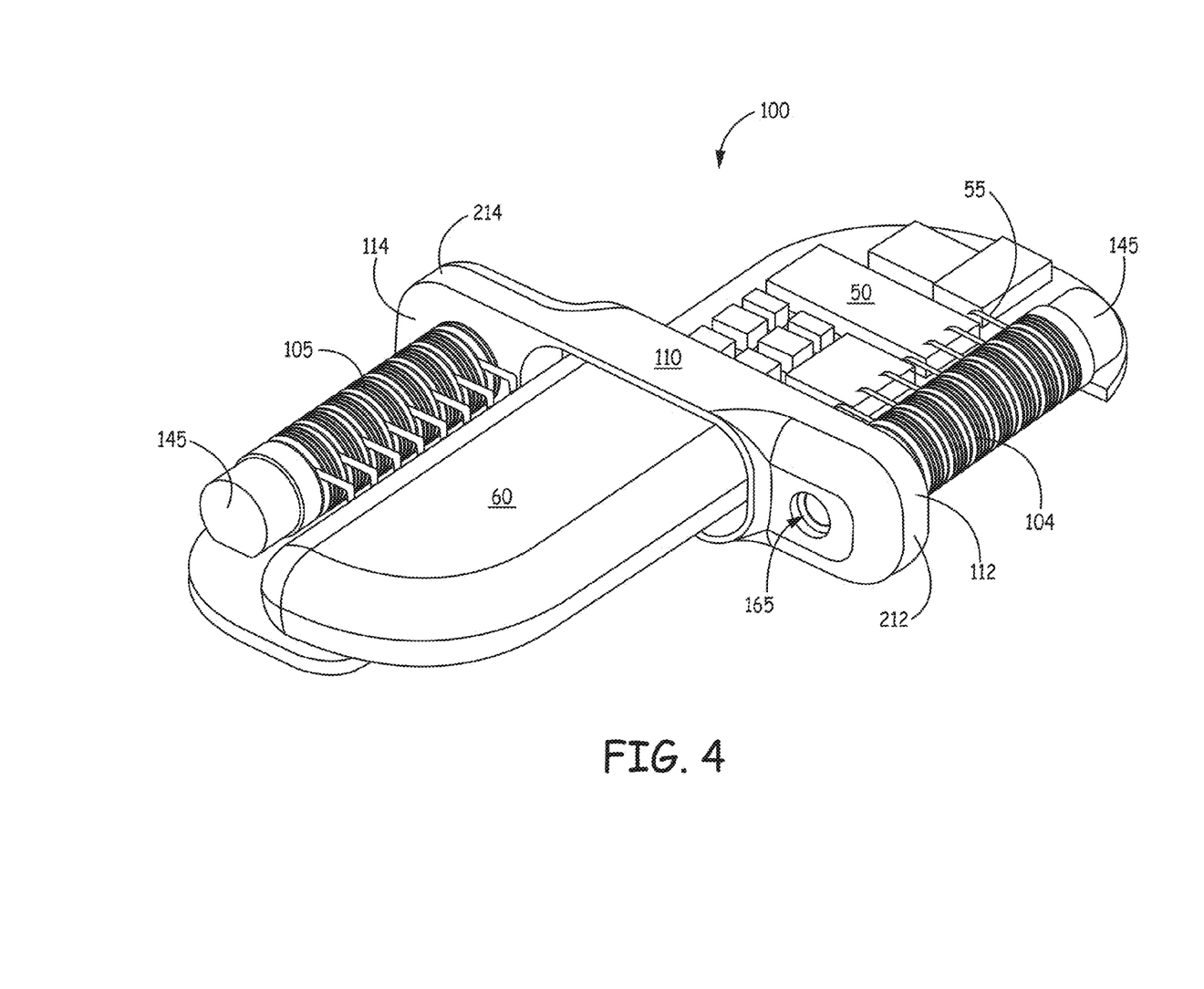
FIG. 4 is a schematic perspective view of implantable active medical device of FIG. 2 with the hermetic housings removed for illustration.

FIG. 2 is a schematic perspective view of an implantable active medical device 100 with opposing internal hermetic lead connectors 104, 105 within the hermetic housings 70 (with the second hermetic housing 71 removed in FIG. 2 for ease of illustration of the internal features). FIG. 3 is a schematic perspective view of the implantable active medical device 100 of FIG. 2 with the hermetic housings 70, 71 in place and two leads 222, 223 engaged with the lead connectors 104, 105. FIG. 4 is a schematic perspective view of implantable active medical device 100 of FIG. 2 with the hermetic housings removed for illustration.

In many embodiments, an implantable active medical device 100 includes a chassis plate 110 having a first major surface 112 and an opposing second major surface 114 and extending between a chassis first end region 212 and a chassis second end region 214. In many embodiments, the chassis plate 110 has a substantially planar first major surface 112 and/or a substantially planar opposing second major surface 114. In many of these embodiments, the substantially planar first major surface 112 and substantially planar opposing second major surface 114 are parallel with each other. In some embodiments the chassis plate 110 has a substantially non-planar first major surface 112 and/or a substantially non-planar opposing second major surface 114. Functional elements of the implantable active medical device are rigidly fixed to the chassis plate to maintain displacement between functional elements. The chassis element or plate 110 can be formed of a metal or other rigid structural material. In many embodiments the chassis element or plate 110 can be formed of titanium or a titanium alloy. In many embodiments, the thickness (distance between the first major surface 112 and an opposing second major surface 114) is in a range of about 1 to 10 mm or from about 4 to 8 mm.

A first elongate lead connector 104 is fixed or hermetically fixed or sealed to the first major surface 112 and extends orthogonally away from the first major surface 112. A second elongate lead connector 105 is fixed to the second major surface 114 and extends orthogonally away from the second major surface 114. A first hermetic housing 70 defines a first sealed housing cavity. The first hermetic housing 70 is fixed or hermetically fixed or sealed to the first major surface 112 or chassis element or plate 110 such as, by laser welding, for example. The first elongate lead connector 104 is disposed within the first sealed housing cavity. A second hermetic housing 71 defines a second sealed housing cavity. The second hermetic housing 71 fixed or hermetically fixed or sealed to the second major surface 114 or chassis plate or element 110. The second elongate lead connector 105 is disposed within the second sealed housing cavity. In many embodiments the first elongate lead connector 104 is fixed to the chassis first end region 212 and the second elongate lead connector 105 is fixed to a chassis second end region 214.

In many embodiments, the first elongate lead connector 104 extends away from the chassis first major surface 112 in a first direction and the second elongate lead connector 105 extends away from the chassis second major surface 114 in a second direction that opposes the first direction. In many embodiments, the first elongate lead connector 104 is parallel and offset or parallel and laterally offset with the second elongate lead connector 105. In many embodiments, the first elongate lead connector 104 is coplanar with the second elongate lead connector 105.

In many embodiments, the implantable active medical device 100 includes electronics 50 fixed to the chassis plate or element 110 and disposed within the first or second hermetic housing 70, 71. Electronics can be any useful electronics such as a circuit board. A circuit board can include both a printed circuit board (often a rigid printed circuit board) and a flexible circuit (also known as a flex circuit), or a combination of a printed circuit board and a flex circuit. In many embodiments a circuit board 50 is fixed to the first major surface 112 of the chassis plate 110 and the circuit board 50 extends orthogonally away from the first major surface 112 and the circuit board 50 is fixed to the first elongate lead connector 104 via interconnects 55 and the circuit board 50 is disposed within the first hermetic or sealed housing 70. A first hermetic housing 70 defines a housing cavity. The first hermetic housing 70 is hermetically fixed to the first major surface 112 or chassis plate 110. The first elongate lead connector 104 and the circuit board 50 are disposed within the first housing cavity. In many embodiments the first hermetic housing 70 is a metallic shell.

In many embodiments the first elongate lead connector 104 is coextensive with the circuit board 50. In many embodiments the first elongate lead connector 104 is fixed to the circuit board 50. In some embodiments the elongate lead connector 104 is fixed to the circuit board 50 via direct electrical connections 55 between the first elongate lead connector 104 and the circuit board 50 as illustrated in FIG. 2. The electronics 50 generally control the active medical device. In some embodiments, the electronics 50 includes memory. The memory can be any magnetic, electronic, or optical media, such as random access memory (RAM), read-only memory (ROM), electronically-erasable programmable ROM, flash memory, or the like. The functional elements can be independently fixed to the first major surface 112 or the opposing second major surface 114 in any arrangement, other than the configuration illustrated in the figures.

In many embodiments the elongate lead connectors 104, 105 are fixed at only one end (proximal end 201) to the chassis plate 110. In these embodiments, the elongate lead connectors 104, 105 are in cantilever arrangement within the hermetic enclosure of the hermetic housings 70, 71.

In many embodiments the implantable active medical device 100 includes a power source 60 fixed to the chassis plate or element 110 and disposed within the first or second hermetic housing 70, 71. In many embodiments, the power source 60 is fixed to the second major surface 114 and disposed within disposed within the second hermetic or sealed housing 71. A second hermetic housing 71 defines a housing cavity. The second hermetic housing 71 is fixed to the second major surface 114 or chassis plate 110. The second elongate lead connector 105 and the power source 60 are disposed within the second housing cavity. In many embodiments the second hermetic housing 71 is a metallic shell.

The power source 60 can include a battery, for example disposed within a hermatic shield or shell. In some embodiments the chassis 110 enables the use of a number of different batteries having different sizes or capacities or configurations as required by different therapy indications. The power source 60 can be electrically connected to the circuit board 50 through the chassis plate 110 via electrical interconects. The power source 60 can be any useful battery or inductive coil.

Figure 5:
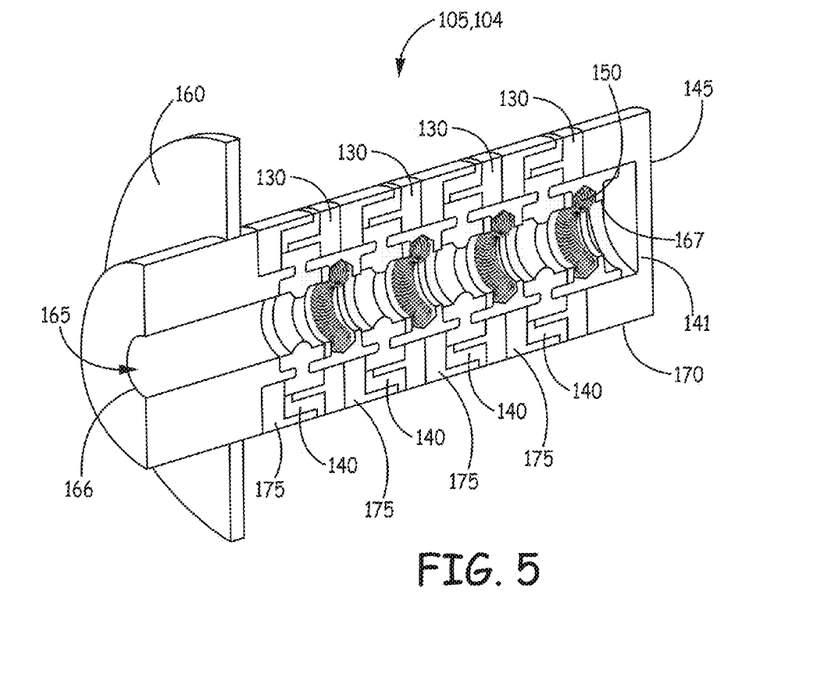
FIG. 5 is a perspective cross-sectional view of the illustrative lead connector.

FIG. 5 is a perspective cross-sectional view of the illustrative lead connector. The illustrated lead connectors 104, 105 are elongate members extending between a lead aperture 165 first open end and an end cap 145, and having an inner surface defining an open lumen lead aperture 165. The elongate lead connector 104, 105 defines at least a portion of the hermetic barrier. The lead connector 104, 105 can be utilized to provide the hermetic barrier extending into a device.

In many embodiments, the lead connector 104, 105 includes one or more subassemblies that include two electrically conducting contact rings 130 and 175 spaced apart by electrically insulating material 140. The electrically insulating material 140 provides a hermetic bond between contact rings 130 and 175. Multiple subassemblies may be joined together such as laser welding to form a hermetic tube, by welding adjacent electrically conducting contact rings together. The two or more electrically conducting contact rings 130, 175 provide electrical communication between the electronics or circuit board 50 and the lead contact 150. The lead connector 105 provides a hermetic seal between the sealed housing 70 interior and the lead aperture 165.

The electrically conducting contact rings can be formed of any useful electrically conductive material and also form a hermetic barrier. In many embodiments, the electrically conducting contact rings are formed of a metallic material such as, for example, titanium, stainless steel, MP35N, niobium, tantalum, platinum, and alloys or combinations thereof. In some embodiments, the electrically conducting contact rings are formed of a metallic material such as, for example, titanium.

The electrically insulating material 140 can be formed of any useful electrically insulating material. In many embodiments the electrically insulating material 140 is a ceramic or glass material. Glass for formation of electrical insulating member 140 includes boro-alumino, boro-alumino silicate and/or boro silicate type glasses. The element(s) and/or compounds used to form electrical insulating member 140 are selected in a manner to reduce tensile stresses with conducting contact rings 130. For example, electrical insulating member 140, employing glass, has a coefficient of thermal expansion (CTE) value about equivalent to or within 15% of the CTE associated with conducting contact rings 130.

In some embodiments, a filtering capacitor is disposed between the electrically conducting contact rings 130, 175 and the electronics 50. The filtering capacitor can effectively filter out undesirable electromagnetic interference (EMI) from the active medical device 100.

Placement of the lead connector 104, 105 within the hermetically sealed active medical device housing enables a direct electrical connection between the lead connector 104, 105 and the electronics 50. In addition, the elimination of a traditional feedthrough and lead connector header can reduce the size and volume of the implantable active medical device and can also reduce the number of parts and connections needed to assemble the implantable active medical device. The chassis plate provides rigid support structure that maintains/minimizes the displacement between components fixed to the chassis element and provides access to at least two sides of the functional elements within the device.

The illustrated lead connector 104, 105 is an elongate member extending between a lead aperture 165 first open end 166 and end cap 145, and having an inner surface 167 defining an open lumen lead aperture 165. The open lumen lead aperture 165 or lead receptacle 165 is configured to accept one lead or lead extension, as described above, and electrically couple one or more lead contacts with one or more connector contacts 150 nested in the elongate body of the lead connector 105, that in many embodiments is generally cylindrical.

In many embodiments, the lead aperture 165 is a cylindrical open lumen of generally circular cross-sectional area formed by an inner surface of the electrically conducting rings 130, 175 and electrically insulating rings 140 bonded together in axial alignment. The lead connector 104, 105 defines a lead connector outer surface 170 and at least a portion of the lead connector outer surface 170 is disposed within the sealed housing 70 interior. In many embodiments, at least a majority of the lead connector outer surface 170 is disposed within the sealed housing 70, 71 interior. In many embodiments, substantially the entire lead connector outer surface 170 is disposed within the sealed housing 70, 71 interior and at least partially defines the sealed housing 70, 71 interior. In some embodiments, the entire lead connector outer surface 170 is disposed within the sealed housing 70, 71 interior.

In the illustrated embodiment, the lead connector 104, 105 is formed of one or more electrically conducting contact rings 130, 175 spaced apart by electrically insulating rings 140. The one or more electrically conducting contact rings 130, 175 are in electrical communication with the electronics (described above), and the lead connector 104, 105 body provides a hermetic seal between the sealed housing interior/lead connector outer surface 170 and the lead aperture 165. The one or more electrically conducting contact rings 130, 175 and electrically insulating rings 140 are assembled in axial alignment to form the lead connector 104, 105. The electrically insulating rings 140 can provide structural integrity and/or a hermetic bond between 130 and 175. Adjacent 130 and 175 rings are then joined typically by laser welding The one or more electrically conducting contact rings 130, 175 can include one or more additional contact elements in electrical contact with and optionally disposed within each of the one or more electrically conducting contact rings 130, 175. These one or more additional contact elements are configured to provide electrical communication between one or more electrically conducting contact rings 130, 175 and a lead contact received within the lead aperture 165. In many embodiments, these contact elements are electrically conductive and resilient to provide an interference fit between the electrically conducting contact ring 130, 175 and lead contact received within the lead aperture 165.

Examples of contact elements include, but are not limited to, spring elements. In many embodiments, the contact element includes an annular helical coil 150 (i.e., continuous coil spring 150) is disposed adjacent an inner surface of the electrically conducting contact ring 130. The helical annular coil 150 can be formed of any useful electrically conductive material such as, for example, a metal like gold, silver, platinum, titanium and the like. When a lead in inserted into the lead aperture 165, the lead and lead contact(s) can deflect the annular helical coil 150 and form an electrical contact between the lead contact and the electrically conducting contact ring 130. The continuous coil spring 150 provides a frictional electrical and mechanical engagement with a lead contact and the adjacent electrically conducting contact ring 130.

A seal element may also be included in 105 aperture to provide electrical isolation between contacts 150 and/or between lead contacts when a lead is inserted into the lead aperture 165. The seal element can be any useful electrically insulating material such as elastomeric material or polymeric material. The seal element can be an annular element that is disposed between the electrically conducting contact rings 130, 175.

A mounting flange 160 can be fixed to the lead connector 104, 105 adjacent the open end 166. The mounting flange 160 can be brazed or welded to the chassis element 110. In many embodiments, the mounting flange 160 can be brazed or welded to the chassis element 110 first major surface 112 or opposing second major surface 114. A retention member (not shown) such as for example, a set screw, can be disposed on the lead connector 104, 105 adjacent to the open end 166 and can assist in mechanical retention of the lead disposed within the lead aperture 165.

The lead connector 104, 105 can be formed by any useful method. In many embodiments, the lead connector 104, 105 is formed by assembling two or more lead connector subassemblies 106. Each lead connector subassembly can be arranged in axial alignment and bonded utilizing a metal to metal bonding technique such as, laser welding, for example, to form the lead connector 104, 105. Each lead connector subassembly includes the electrically insulating ring 140 fixed between the electrically conducting contact ring 130 and an attachment ring or electrically conducting spacer ring 175. Thus, the electrically conducting spacer ring 175 is affixed to a first side of the electrically insulating ring 140 and the electrically conducting contact ring 130 is affixed to a second opposing side of the electrically insulating ring 140. The lead connector subassembly includes the electrically insulating ring 140 bonding the electrically conducting contact ring 130 to the electrically conducting spacer ring 175. The electrically insulating ring 140 is integral to the hermetic seal between the sealed housing interior/lead connector outer surface 70 and the lead aperture 165.

The electrically conducting spacer ring 175 can be formed of any useful electrically conductive material. In many embodiments, the electrically conducting spacer ring 175 is formed of a metallic material such as, for example, titanium, stainless steel, MP35N, niobium, tantalum, platinum, and alloys or combinations thereof. In some embodiments, the one electrically conducting spacer ring 175 is formed of a metallic material such as, for example, titanium.

Thus, embodiments of the IMPLANTABLE DEVICE WITH OPPOSING LEAD CONNECTORS are disclosed. The implementations described above and other implementations are within the scope of the following claims. One skilled in the art will appreciate that the present disclosure can be practiced with embodiments other than those disclosed. The disclosed embodiments are presented for purposes of illustration and not limitation, and the present invention is limited only by the claims that follow.

What is claimed is:

1. An implantable active medical device comprising:
   a chassis plate having a first major surface and an opposing second major surface and extending between a chassis plate first end region and a chassis plate second end region;
   a first elongate lead connector fixed to the first major surface and extending orthogonally away from the first major surface;
   a second elongate lead connector fixed to the second major surface and extending orthogonally away from the second major surface;
   a first hermetic housing defining a first sealed housing cavity, the first hermetic housing fixed to the first major surface and the first elongate lead connector is disposed within the first sealed housing cavity; and
   a second hermetic housing defining a second sealed housing cavity, the second hermetic housing fixed to the second major surface and the second elongate lead connector is disposed within the second sealed housing cavity.

2. The implantable active medical device according to claim 1, wherein the first elongate lead connector comprises a closed end, an open end hermetically joined to the first major surface of the chassis plate, an outer surface at least partially defining the first sealed housing cavity, and an inner surface defining a first lead aperture, and the second elongate lead connector comprises a closed end, an open end hermetically joined to the second major surface of the chassis plate, an outer surface at least partially defining the second sealed housing cavity, and an inner surface defining a second lead aperture.

3. The implantable active medical device according to claim 1, wherein the first elongate lead connector extends away from the chassis first major surface in a first direction and the second elongate lead connector extends away from the chassis second major surface in a second direction that opposes the first direction.

4. The implantable active medical device according to claim 1, wherein the first elongate lead connector is fixed to the chassis first end region and the second elongate lead connector is fixed to a chassis second end region of the chassis plate.

5. The implantable active medical device according to claim 1, further comprising a circuit board fixed to the first elongate lead connector and the first major surface and disposed within the first sealed housing cavity.

6. The implantable active medical device according to claim 5, wherein the first elongate lead connector is coextensive with the circuit board.

7. The implantable active medical device according to claim 1, further comprising a power source fixed to the second major surface and disposed within the second sealed housing cavity.

8. The implantable active medical device according to claim 7, wherein the power source is electrically coupled to a circuit board through the chassis.

9. The implantable active medical device according to claim 1, wherein the first major surface and the second major surface are parallel to each other.

10. The implantable active medical device according to claim 1, wherein the first elongate lead connector is parallel and offset with the second elongate lead connector.

11. The implantable active medical device according to claim 1, wherein the first elongate lead connector is coplanar with the second elongate lead connector.

12. An implantable active medical device comprising:
    a chassis plate having a first major surface and an opposing second major surface and extending between a chassis plate first end region and a chassis plate second end region;
    a first elongate lead connector fixed to the first major surface and extending orthogonally away from the first major surface;
    a second elongate lead connector fixed to the second major surface and extending orthogonally away from the second major surface;
    a first housing defining a first housing cavity and a power source located within the first housing cavity, the first housing fixed to the first major surface and the power source and the first elongate lead connector is disposed within the first housing cavity; and
    a second housing defining a second housing cavity and a circuit board located within the second housing cavity, the second housing fixed to the second major surface and the circuit board and the second elongate lead connector is disposed within the second housing cavity.

13. The implantable active medical device according to claim 12, wherein the first elongate lead connector comprises a closed end, an open end hermetically joined to the first major surface of the chassis plate, an outer surface at least partially defining the first housing cavity, and an inner surface defining a first lead aperture, and the second elongate lead connector comprises a closed end, an open end hermetically joined to the second major surface of the chassis plate, an outer surface at least partially defining the second housing cavity, and an inner surface defining a second lead aperture.

14. The implantable active medical device according to claim 12, wherein the first elongate lead connector and the second elongate lead connector extends away from the chassis in opposing directions.

15. The implantable active medical device according to claim 12, wherein the first elongate lead connector is hermetically fixed to the chassis first end region and the second elongate lead connector is hermetically fixed to a chassis second end region of the chassis plate.

16. The implantable active medical device according to claim 12, wherein the first major surface and the second major surface are parallel to each other.

17. The implantable active medical device according to claim 12, wherein the first elongate lead connector is parallel and offset with the second elongate lead connector.

18. The implantable active medical device according to claim 12, wherein the first elongate lead connector is coplanar with the second elongate lead connector.

19. The implantable active medical device according to claim 12, wherein the power source is electrically coupled to the circuit board through the chassis.

* * * * *